United States Patent
Anderson et al.

(10) Patent No.: US 6,760,624 B2
(45) Date of Patent: Jul. 6, 2004

(54) METHOD AND APPARATUS FOR MEASURING LEAD IMPEDANCE IN AN IMPLANTABLE CARDIAC RHYTHM MANAGEMENT DEVICE

(75) Inventors: Russell E. Anderson, Marine on St. Croix, MN (US); David J. Yonce, Fridley, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 373 days.

(21) Appl. No.: 10/006,457

(22) Filed: Dec. 3, 2001

(65) Prior Publication Data

US 2003/0105500 A1 Jun. 5, 2003

(51) Int. Cl.[7] .............................................. A61N 1/375
(52) U.S. Cl. ........................................................ 607/28
(58) Field of Search ................................ 607/8, 27, 28, 607/30, 4, 62, 63; 600/547, 506

(56) References Cited

U.S. PATENT DOCUMENTS

| | | | | |
|---|---|---|---|---|
| 5,201,865 A | * | 4/1993 | Kuehn | 607/8 |
| 5,741,311 A | | 4/1998 | McVenes et al. | |
| 5,897,577 A | * | 4/1999 | Cinbis et al. | 607/28 |
| 6,044,294 A | | 3/2000 | Mortazavi et al. | |
| 6,104,954 A | * | 8/2000 | Blunsden | 607/8 |
| 6,317,633 B1 | * | 11/2001 | Jorgenson et al. | 607/28 |

* cited by examiner

Primary Examiner—George Manuel
(74) Attorney, Agent, or Firm—Nikolai & Mersereau, P.A.; Thomas J. Nikolai

(57) ABSTRACT

A method and apparatus for measuring the lead impedance of a medical lead used with an implantable medical stimulator which relies upon a count of the number of switching cycles of a switching converter power supply to replenish the energy delivered from an pacing capacitor in delivering a stimulating pulse to tissue.

11 Claims, 2 Drawing Sheets

METHOD AND APPARATUS FOR MEASURING LEAD IMPEDANCE IN AN IMPLANTABLE CARDIAC RHYTHM MANAGEMENT DEVICE

BACKGROUND OF THE INVENTION

I. Field of the Invention

This invention relates generally to cardiac stimulating apparatus, and more particularly to a method and apparatus for continuous measurement of the impedance presented to the implanted pulse generator apparatus by a pacing and/or defibrillating lead.

II. Discussion of the Prior Art

Although many implantable cardiac rhythm management systems provide data concerning lead function, including pulse voltage, current, charge and energy, the measurement that is used most frequently is that of lead or stimulation resistance (impedance). Changes in lead impedance affect the other measures of lead function.

The terms "resistance" and "impedance", although technically different, are often used interchangeably by the clinical community. Impedance is a complex concept reflecting a changing environment involving a variety of factors. This results in fluctuations in the moment-to-moment resistance. The resistance to electron flow in a pacing system progressively rises during the delivery of the stimulation pulse as a result of polarization at the electrode-tissue interface and, as a continuously changing variable, is appropriately termed impedance. The actual resistance to current flow imparted by the conductor coil is fixed and represents a small portion of the total stimulation resistance. The polarization at the electrode-tissue interface, which is due in part to the surface area and geometry of the electrode, and the impedance associated with conduction of the pulse through the body's tissues play a larger role in the overall resistance of the system. All this is incorporated in the single measurement termed either lead impedance, or more accurately, stimulation impedance.

Stimulation impedance is affected by many factors, not the least of which are electrode size, configuration and materials. Manufacturers have designed electrodes with high impedance values. For any given output, a high impedance system reduces the overall current drain of the battery and effectively increases the unit's longevity. Other leads have been designed with low polarization to allow for detection of capture with each pace stimulus. Polarization and impedance are not same phenomenon, although one affects the other. For any given lead model, there is a range of normal impedance values that may be broad, whereas for a specific lead within that model series, the impedance should fall within a relatively narrow range.

The clinician can use knowledge of the lead impedance to follow and identify a developing mechanical problem with the lead. This requires baseline or historical data to recognize subtle changes that may reflect a conductor fracture or a breach of the insulation. It is essential to know what device is being used to make these measurements. As noted previously, different devices may obtain these data at different points of the pacing stimulus. Because of these differences, the impedance measurement obtained with a pacing system analyzer at the time of implantation may be significantly different from that obtained by telemetry from the implanted pacemaker moments, if not years, later. This difference does not necessarily imply a problem. Furthermore, impedance may evolve over time, with a fall in impedance occurring in the days to weeks after implantation, followed by a gradual rise toward the initial measurements on a chronic basis.

Multiple factors may affect impedance, particularly in a unipolar system. For example, measurements obtained during deep inspiration may significantly differ from those obtained during maximal exhalation. In the same patient, impedance measurements obtained that are based on a single output pulse may vary by 100 ohms or even more during the same follow-up evaluation while remaining consistent with normal function. If a marked change in lead impedance from previous measurements (e.g., more than 300 ohms) is encountered during a routine follow-up evaluation, further evaluation of the pacing system is advisable, although even these changes may be normal. If the patient has no clinical symptoms and has stable capture and sensing thresholds, operative intervention would be premature, although a more frequent follow-up schedule might be prudent. A dramatic change in the telemetered lead impedance in the presence of a clinical problem, however, directs the physician toward the likely source of the difficulty.

A dramatic fall in impedance may reflect a break in the insulation, especially in the case of a unipolar lead. This effectively increases the surface area of the electrode, resulting in lower impedance. In a unipolar system, an insulation problem provides an alternative pathway for current flow, starting closer to the pulse generator and resulting in less energy reaching the heart, possibly causing loss of capture. The amplitude of the stimulus artifact, as recorded by an ECG, is determined by the distance the current travels in the tissue from the cathode (tip electrode) to anode (ring electrode or housing of the pulse generator). Hence, a bipolar pacing system in which both active electrodes are inside the heart, separated by only one to two centimeters, results in a small stimulus artifact, whereas the pacing spike recorded in a unipolar system, in which the current travels from the tip electrode to the housing of the pulse generator is large despite equivalent output settings. It is also affected by the recording system: some of the newer digital designs result in a marked signal-to-signal variation in amplitude or in the generation of a uniform amplitude artifact, with any high-frequency electrical transient precluding differentiation of a bipolar and unipolar pacing system based on the analysis of the ECG recording.

In a previously stable cardiac rhythm management system, a mechanical problem developing with the lead—either a breach in the insulation or a conductor fracture—results in a change in the stimulation impedance, which may be reflected by a change in the ECG recorded stimulus artifact. In a bipolar pacing system, an insulation defect between the proximal conductor and the tissue of the body is not likely to affect capture thresholds, but it results in a larger stimulus artifact, making it appear unipolar. Depending on the actual location of the insulation fracture in either the bipolar or unipolar lead, stimulation of the extra cardiac muscle contiguous to the insulation defect may occur. Insulation fractures may also attenuate the electrical signal reaching the pacemaker, possibly resulting in sensing failure.

An increase in lead impedance may be the result of a conductor fracture or a connector problem. When this occurs, the lead impedance often rises to high levels. It is inappropriate, however, to assume that a normal lead impedance is 500 ohms. New leads are being introduced that are designed to be high impedance with values ranging from 1500 to 2500 ohms. Other leads, at implantation, have a relative impedance level in the range of 300 ohms and even 200 ohms. Thus, it is essential to look for a trend in serial lead impedance measurements in conjunction with the stability or changes in capture and sensing thresholds. A mechanical problem with the lead—either a conductor fracture resulting in a high impedance or an insulation failure resulting in a low impedance—eventuates in an overall clinical problem that can be identified by telemetric measurement of the stimulation impedance. When the impedance is sufficiently high, there is no current flow and no effective output, although the telemetered event markers indicate an output and therefore loss of capture. The reduced current flow also results in a fall in the measured current drain of the battery. Any problem, however, may be intermittent. This typically occurs when the two broken ends make contact at times but are separated at other times, or in the case of an insulation failure, when lead movement either opens the compromised area or pushes the edges of the break together resulting in normal function.

Some prior art pacemakers have been able to report lead impedance measurements on a beat-by-beat basis, allowing the physician to observe the digital read-out of lead impedance on a programmer's screen over a protracted number of cycles. However, such systems have been wasteful of battery current. Here, reference is made to U.S. Pat. No. 5,741,311, which requires application of an AC drive current burst after each pacing pulse.

It can be seen from the foregoing, then, that assessment of lead integrity is essential to patient care and every implant or follow-up evaluation of an implanted device should include a review of such lead integrity by appropriate lead impedance measurement.

Historically, there has been a great deal of overhead associated with making lead impedance measurements. Typically, dedicated sampling networks and algorithms are used to provide a measure of lead impedance by forcing a known signal through the lead-tissue interface and measuring the resultant voltage across the lead terminals. Such methods require significant amounts of analog and digital circuitry and include firmware and software complexities. Moreover, there is an impact to manufacturing and test, since shifts in processed parameters frequently reduce product yield or cause a reassessment of test limits. As an example, reference is made to U.S. Pat. No. 6,044,294.

A need, therefore, exists for a method to measure lead impedance without requiring additional dedicated circuitry to obtain the measurement. The method described herein provides accurate impedance measurement results with a minimum of overhead to the implanted device and programmer. This allows for the addition of other features within the pulse generator for the same given device size. That is, the method of the present invention allows a reduction in circuitry/firmware while permitting accurate impedance measurements to be obtained.

SUMMARY OF THE INVENTION

The instant invention provides a new apparatus and method for measuring the impedance of a medical lead used in combination with an implantable pulse generator of the type including a battery-powered switching converter that delivers electrical energy to a pacing capacitor where the pulse generator's stimulating output pulse is periodically delivered from the pacing capacitor. Logic in the pulse generator is arranged to tally a number of switching cycles of the switching converter that is needed to replenish the energy removed from the pacing capacitor upon delivery of a stimulating pulse to the cardiac tissue. An algorithm is then executed in which lead impedance can be determined as a function of the tally of the number of switching cycles needed to replenish the energy removed from the pacing capacitor upon delivery of the stimulating pulse to the cardiac tissue.

DESCRIPTION OF THE PREFERRED EMBODIMENT

Figure 1:
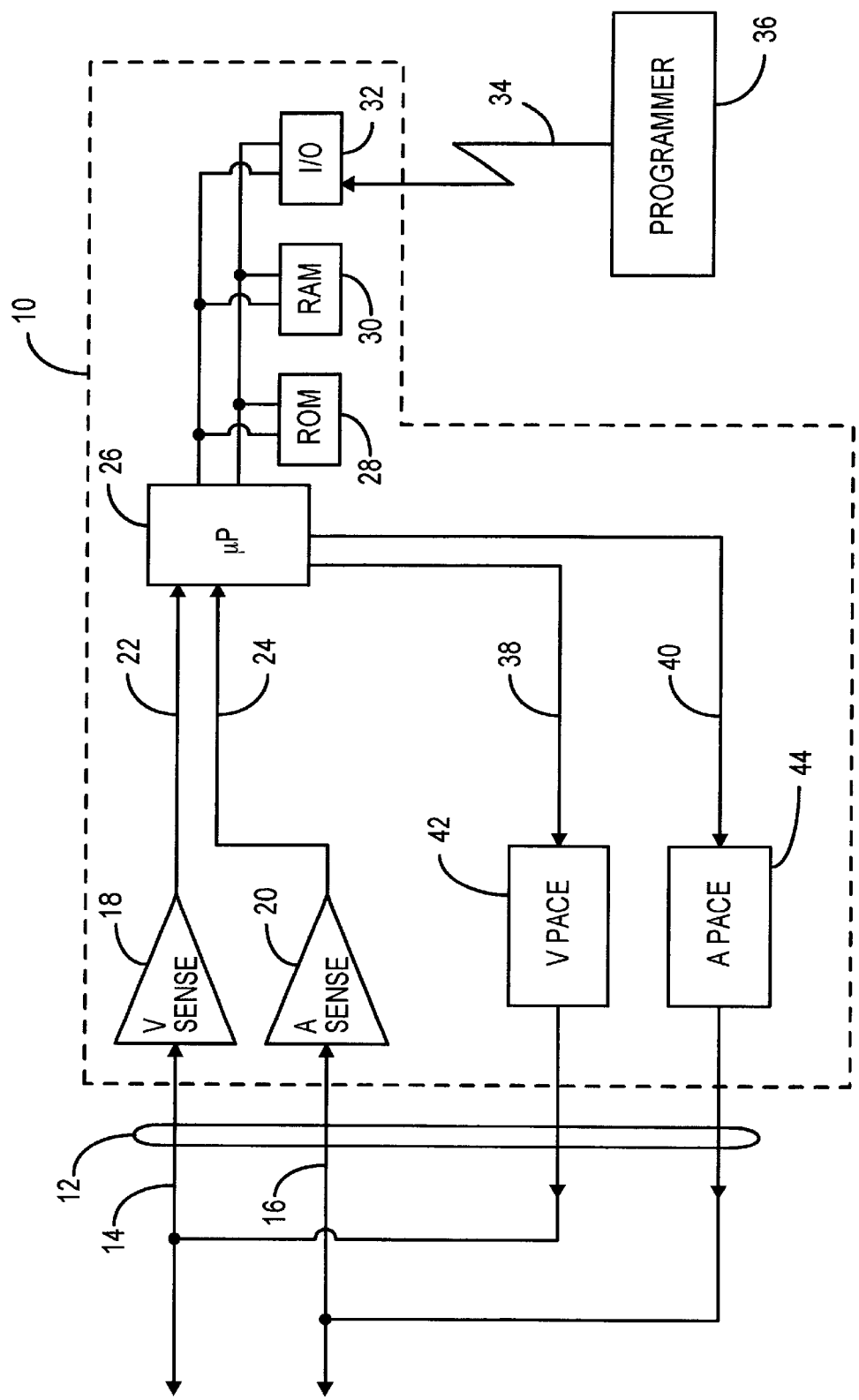
FIG. 1 is a general block diagram of a typical implantable cardiac rhythm management device in which the present invention finds use.

Referring initially to FIG. 1, there is shown enclosed by the dashed line box 10 one embodiment of an implantable cardiac rhythm management device. It is adapted to be connected by a medical lead 12 to targeted cardiac tissue. As is well known in the art, a typical lead includes a plurality of elongated electrical conductors embedded in an elongated, flexible, insulating lead body and connected electrically to electrodes (not shown) located on the surface of the lead body at or near its distal end and to lead terminals at its proximal end.

The electrodes proximate the distal end of the lead body are appropriately placed relative to the heart so that ventricular depolarization signals and atrial depolarization signals are fed back over lead conductors 14 and 16 to the input of ventricular sense amplifier 18 and atrial sense amplifier 20. These sense amplifiers include wave shaping and thresholding circuitry whereby R-waves and P-waves in an electrogram can be applied, via conductors 22 and 24, as inputs to a controller 26. The controller 26 may be microprocessor-based, as shown, or may include a finite state machine architecture or even combinatorial logic circuitry. Where a microprocessor-based controller is used, there is also associated with it, a ROM device 28, a RAM device 30 and an input/output controller 32. The ROM comprises a memory for storing a program of instructions executable by the microprocessor of controller 26. The RAM memory 30 is arranged to store programmable operands and other data used in the execution of the instruction stored in ROM 28. The I/O module 32 interfaces the microprocessor of controller 26 with a telemetry link 34 leading to an external programmer 36.

The microprocessor-based controller 26 provides control signals, via conductors 38 and 40, to a ventricular pulse generator 42 and an atrial pulse generator 44, respectively, associated with the right side of the heart. The device may also include pulse generators for effecting stimulation of the left ventricle and left atrium. At precise times determined by the microprocessor-based controller 26, the ventricular pulse generator 42 and/or the atrial pulse generator 44 deliver cardiac stimulating pulses to the heart, via the distal electrodes on the lead 12.

Figure 2:
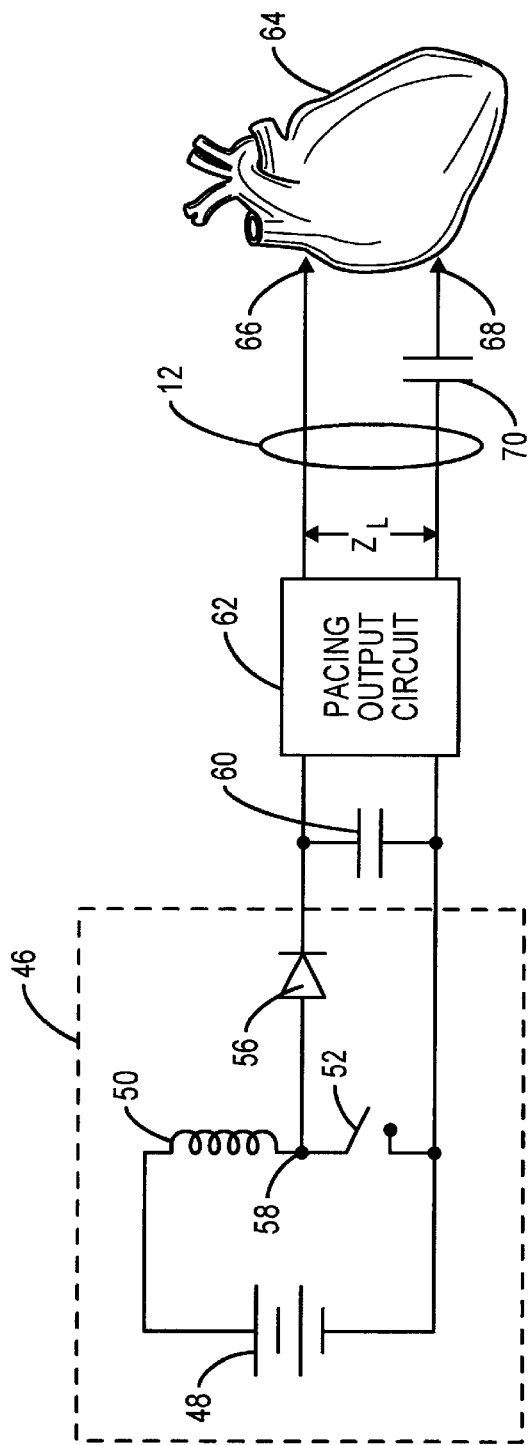
FIG. 2 is a schematic electrical diagram of the pulse generator portion of the implantable device of FIG. 1.

Referring next to FIG. 2, there is illustrated a schematic electrical diagram of the ventricular pulse generator 42. This same circuitry may be utilized in implementing the atrial pace pulse generator 44. Further, the cardiac rhythm management device may incorporate the same type of pulse generator for stimulating the left side of the heart. It is seen to comprise a switching converter that is shown as being enclosed by the broken line box 46 and it includes a battery supply 48 that is connected in parallel with a series combination of an inductor 50 and a semi-conductor switch 52. A diode 56 is connected between a junction 58 between the inductor 50 and the switch 52. The on/off state of the switch 52 is controlled by the microprocessor-based controller 26 in FIG. 1. The switching converter 46 is arranged to deliver energy to an pacing capacitor 60.

Considering operation to start when switch 52 is opened, switch 52 is first closed, such that the input battery voltage from battery 48 is placed directly across the inductor 50. This causes the current to ramp upward in a linear fashion from zero to some peak value and have energy stored within the magnetic field of the inductor 50 proportional to the square of this peak current value ($E=\frac{1}{2}Li^2$). Since the junction 58 between the inductor 50 and the anode of the diode 56 are effectively connected to ground because switch 52 is closed, the diode is back-biased and no load current passes through the inductor during this period.

When the switch 52 opens, the inductor voltage reverses polarity and the output side (junction 58) flies back above the input voltage and is clamped by the diode 56 at the output voltage. The current then begins to linearly ramp downward until the energy within the magnetic field of the inductor is completely depleted. Hence, the output voltage developed across the pacing capacitor 60 is greater than the battery input voltage.

Figure 3:
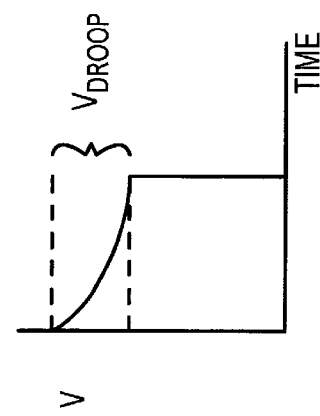
FIG. 3 is a waveform illustrating the voltage developed across the load comprising a stimulating pulse.

To fully charge the pacing capacitor 60 to a desired voltage state may require several switching cycles of the switch 52. At times determined by the microprocessor-based controller 26, the pacing output circuit 62 connects the capacitor 60 across the terminals of the lead 12 to deliver stimulating energy to the heart 64, via electrodes 66–68 FIG. 3 illustrates the wave shape of the pacing supply voltage vs. time. The energy stored in the capacitor when charged to a voltage, v, is $E_c=\frac{1}{2}Cv^2$. Thus, the energy delivered to the load, upon actuation of the pacing output circuit 62, is directly related to the voltage droop shown in FIG. 3. Further, the energy needed to replenish the energy to the pacing capacitor 60 is directly proportional to the number of switching cycles of the switching converter 46 needed to recharge the pacing capacitor 60.

Stated otherwise, a measure of the energy delivered by a pacing pulse can be determined by counting the number of switching cycles necessary to replenish the pacing supply capacitor 60 following delivery of a paced pulse. The total amount of energy loss is then obtained by the product of the switching cycle counter and the energy per switching cycle delivered by the converter 46. The energy per cycle is a function of the DC to DC converter 46, and can either be constant over the range of possible voltages, or may vary as a function of battery voltage. If constant, the multiplier value does not change over the operating voltage range. If variable, the energy per switching cycle can be characterized by means of a "look-up table" developed during testing at the time of manufacture and stored in the RAM memory 30.

As indicated above, the amount of energy delivered to the output circuitry and the heart during a delivery of a pacing stimulus can be found by counting the number of switching cycles needed to recharge the pacing capacitor 60 following the delivery of the paced pulse. Once the energy is known, the lead impedance can be calculated using the following relationship:

$$Z_{lead} = \frac{t_{pace}}{C_T \cdot \ln\left\{1 - \left(\frac{2V_{pace} - 2\sqrt{V^2_{pace} - \frac{2E_{loss}}{C_{pace}}}}{V_{pace}}\right)\right\}}$$

where $t_{pace}$ is the pacing pulse width, $E_{loss}$ is the energy lost from $C_{pace}$ during the pace, $V_{pace}$ is the initial pacing voltage, and $C_T$ is the total capacitance of the pacing capacitor 60 and recharge DC blocking capacitor 70.

The above relationship assumes equal pacing and recharge blocking capacitance values, but those skilled in the art will be able to modify the equation to cover a situation where the two are unequal or if only a pacing supply capacitor is present.

It is recognized that impedances, other than only lead impedance may be presented to the pacing output circuit 62. By proper calibration at the time of manufacture using known loads, and then storing the calibration factors in memory, the true values of the lead impedance itself can be derived from the value calculated using the foregoing equation.

Existing prior art systems typically require dedicated circuitry to measure lead impedance. In addition, those systems requiring application of a high frequency signal to the lead and a resultant current measurement are unnecessarily wasteful of integrated circuit space and battery power. Implementation of the present invention allows extrapolation of lead impedance from information related to pacing supply energy consumption, a parameter that is already monitored in many implantable medical devices. The reduction in integrated circuit area results from the fact that no dedicated analog or digital circuitry is required to obtain the lead impedance measurement. Another advantage of the present invention is the fact it affords the ability to measure lead impedance at any pacing voltage and/or width. It also allows beat-to-beat lead impedance measurements without wasting battery power.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A method for measuring lead impedance in an implantable cardiac rhythm management device, comprising the steps of:

(a) providing an implantable cardiac rhythm management device having a pulse generator with a switching converter type power supply for replenishing energy to a pacing supply capacitor following delivery of a stimulating pulse to cardiac tissue by way of an electrode on a lead coupled to the pulse generator and a microprocessor-based controller coupled in controlling relation to the pulse generator, said microprocessor comprising a counter;

(b) counting a number of switching cycles required by the switching converter to replenish the energy delivered from the pacing supply capacitor in generating the stimulating pulse in said counter; and (c) determining the lead impedance as a function of the number of switching cycles of the switching converter needed to restore the amount of energy delivered from the pacing supply capacitor in generating a preceding stimulating pulse.

2. A method for measuring lead impedance in an implantable cardiac rhythm management device, comprising the steps of:
   (a) providing an implantable cardiac rhythm management device having a pulse generator with a switching convertor type power supply for replenishing energy to a pacing supply capacitor following delivery of a stimulating pulse to cardiac tissue by way of an electrode on a lead coupled to the pulse generator and a microprocessor-based controller coupled in controlling relation to the pulse generator, said microprocessor comprising a counter;
   (b) counting a number of switching cycles required by the switching converter to replenish the energy delivered from the pacing supply capacitor in generating the stimulating pulse in said counter; and
   (c) determining the lead impedance as a function of the number of switching cycles of the switching converter needed to restore the amount of energy delivered from the pacing supply capacitor in generating a preceding stimulating pulse by solving the equation:

$$Z_{lead} = \frac{t_{pace}}{C_T \cdot \ln\left\{1 - \left(\frac{2V_{pace} - 2\sqrt{V^2_{pace} - \frac{2E_{loss}}{C_{pace}}}}{V_{pace}}\right)\right\}}$$

where
   $Z_{lead}$ is the lead impedance;
   $t_{pace}$ is the pulse width of the stimulating pulse;
   $C_{pace}$ is the capacitance of the pacing supply capacitor;
   $C_T$ is the total capacitance of $C_{pace}$ and a capacitance of a blocking capacitor in the pulse generator;
   $V_{pace}$ is the initial pacing voltage; and
   $E_{loss}$ is energy lost from $C_{pace}$ during delivery of the preceding stimulating pulse.

3. The method of claim 2 and further including the step of:
   creating a look-up table in a memory of the cardiac rhythm management device of energy restored to the pacing supply capacitor during each switching cycle of the switching converter versus battery voltage available to the switching converter; and
   computing $E_{loss}$ by multiplying said count of the number of switching cycles by an entry in the look-up table.

4. The method of claim 2 and further including the steps of:
   creating a look-up table in a memory of the cardiac rhythm management device of energy restored to the pacing supply capacitor during each switching cycle of the switching converter versus pacing supply voltage; and
   capturing $E_{loss}$ by multiplying said count of the number of switching cycles by an entry in the look-up table.

5. The method of claim 4 and further including the steps of:
   creating a look-up table in a memory of the cardiac rhythm management device of energy restored to the pacing supply capacitor during each switching cycle of the switching converter versus battery supply voltage and pacing supply voltage; and
   capturing $E_{loss}$ by multiplying said count of the number of switching cycles by an entry in the look-up table.

6. A cardiac rhythm management device comprising:
   (a) a pulse generator including a battery powered switching converter for delivering a pacing supply voltage to a pacing supply capacitor;
   (b) a lead having an electrode thereon and connected to the pulse generator for applying stimulating pulses from the pacing supply capacitor to cardiac tissue;
   (c) controller coupled to the pulse generator for controlling the application of the stimulating pulses from the pacing supply capacitor to the cardiac tissue;
   (d) a counter for tallying a number of switching cycles of the switching converter needed to replenish the energy removed from the pacing supply capacitor upon delivery of a stimulating pulse to the cardiac tissue; and
   (e) said controller being operative to compute the impedance of said lead as a function of a tally accumulated by the counter.

7. A cardiac rhythm management device comprising:
   (a) a pulse generator including a battery powered switching converter for delivering a pacing supply voltage to a pacing supply capacitor;
   (b) a lead having an electrode thereon and connected to the pulse generator for applying stimulating pulses from the pacing supply capacitor to cardiac tissue;
   (c) controller coupled to the pulse generator for controlling the application of the stimulating pulses from the pacing supply capacitor to the cardiac tissue;
   (d) a counter for tallying a number of switching cycles of the switching converter needed to replenish the energy removed from the pacing supply capacitor upon delivery of a stimulating pulse to the cardiac tissue; and
   (e) a telemetry circuit for establishing duplex communication with an external programmer/monitor whereby the tally accumulated by the counter, the battery voltage and the pacing supply voltage are delivered to the external programmer; and
   (f) the programmer/monitor being operative to compute the impedance of said lead at a function of the tally, said battery voltage and said pacing supply voltage.

8. The cardiac rhythm management device of claim 6 wherein the controller is operative to solve the equation:

$$Z_{lead} = \frac{t_{pace}}{C_T \cdot \ln\left\{1 - \left(\frac{2V_{pace} - 2\sqrt{V^2_{pace} - \frac{2E_{loss}}{C_{pace}}}}{V_{pace}}\right)\right\}}$$

where
   $Z_{lead}$ is the lead impedance;
   $t_{pace}$ is the pulse width of the stimulating pulse;
   $V_{pace}$ is the initial amplitude of the stimulating pulse;
   $C_{pace}$ is the capacitance of the pacing supply capacitor;

$C_T$ is the $$\frac{C_{pace} \cdot C_{block}}{C_{pace} + C_{block}}$$

$C_{block}$ is the capacitance of a blocking capacitor; and $E_{loss}$ is energy lost from the pacing capacitor during generation of a stimulating pulse.

9. The cardiac rhythm management device of claim 7 wherein the programmer/monitor is operative to solve the equation:

$$Z_{lead} = \frac{t_{pace}}{C_T \cdot \ln\left\{1 - \left(\frac{2V_{pace} - 2\sqrt{V^2_{pace} - \frac{2E_{loss}}{C_{pace}}}}{V_{pace}}\right)\right\}}$$

where $Z_{lead}$ is the lead impedance;

$t_{pace}$ is the pulse width of the stimulating pulse;

$V_{pace}$ is the initial amplitude of the stimulating pulse;

$C_{pace}$ is the capacitance of the pacing supply capacitor;

$C_T$ is the $$\frac{C_{pace} \cdot C_{block}}{C_{pace} + C_{block}}$$

$C_{block}$ is the capacitance of a blocking capacitor; and $E_{loss}$ is energy lost from the pacing capacitor during generation of a stimulating pulse.

10. The cardiac rhythm management device of claim 6 and further including a memory operatively associated with the controller, said memory containing a look-up table for storing data corresponding to an amount of energy delivery to the pacing supply capacitor during each switching cycle of the switching converter for different levels of battery output voltage and pacing supply voltage.

11. The cardiac rhythm management device of claim 10 wherein $E_{loss}$ is computed by a product of the counter tally and a value stored in the look-up table.

* * * * *